(12) United States Patent
Piironen et al.

(10) Patent No.: US 10,988,392 B2
(45) Date of Patent: Apr. 27, 2021

(54) METHOD AND SYSTEM FOR OPTIMIZATION OF COAGULATION AND/OR FLOCCULATION IN A WATER TREATMENT PROCESS

(71) Applicant: KEMIRA OYJ, Helsinki (FI)

(72) Inventors: Marjatta Piironen, Oulu (FI); Iiris Joensuu, Espoo (FI); Mehrdad Hesampour, Espoo (FI)

(73) Assignee: KEMIRA OYJ, Helsinki (FI)

( * ) Notice: Subject to any disclaimer, the term of this patent is extended or adjusted under 35 U.S.C. 154(b) by 161 days.

(21) Appl. No.: 16/088,749

(22) PCT Filed: Mar. 31, 2017

(86) PCT No.: PCT/FI2017/050229
§ 371 (c)(1),
(2) Date: Sep. 26, 2018

(87) PCT Pub. No.: WO2017/168054
PCT Pub. Date: Oct. 5, 2017

(65) Prior Publication Data
US 2020/0223719 A1    Jul. 16, 2020

(30) Foreign Application Priority Data
Apr. 1, 2016    (FI) .................................... 20165282

(51) Int. Cl.
*C02F 1/52*    (2006.01)
*C02F 1/24*    (2006.01)
(Continued)

(52) U.S. Cl.
CPC .............. *C02F 1/5209* (2013.01); *C02F 1/24* (2013.01); *C02F 1/441* (2013.01); *C02F 1/442* (2013.01);
(Continued)

(58) Field of Classification Search
None
See application file for complete search history.

(56) References Cited

U.S. PATENT DOCUMENTS

| 4,783,269 A | 11/1988 | Baba et al. |
| 2002/0081748 A1 | 6/2002 | Roberts et al. |

(Continued)

FOREIGN PATENT DOCUMENTS

| CN | 1116187 A | 2/1996 |
| CN | 1181747 A | 5/1998 |

(Continued)

OTHER PUBLICATIONS

Office Action (Notice of Grounds for Rejection) dated Feb. 10, 2020, by the Korean Patent Office in corresponding Korean Patent Application No. 10-2018-7031129, and an English Translation of the Office Action. (18 pages).

(Continued)

*Primary Examiner* — Richard C Gurtowski
(74) *Attorney, Agent, or Firm* — Buchanan Ingersoll & Rooney PC

(57) ABSTRACT

Methods and systems are disclosed for optimization of coagulation and/or flocculation in a water treatment process. According to exemplary embodiments, samples are taken from an aqueous liquid and the samples are monitored with an imaging device to capture visual data of particles dispersed or suspended in the liquid. The particles are classified into particle types based on the visual data and a particle size distribution indication is computed for each classified particle type. The particle size distribution indication is then compared to a predetermined particle size distribution value, and in response to a difference detected, dosage of at least one coagulation and/or flocculation agent in the water treatment process can be adjusted.

22 Claims, 12 Drawing Sheets

(51) Int. Cl.
*C02F 1/44* (2006.01)
*C02F 1/56* (2006.01)
*G01N 15/02* (2006.01)
*G01N 15/06* (2006.01)
*G01N 33/18* (2006.01)
*G05B 11/32* (2006.01)
*C02F 1/00* (2006.01)

(52) U.S. Cl.
CPC ............ *C02F 1/444* (2013.01); *C02F 1/5245* (2013.01); *C02F 1/5263* (2013.01); *C02F 1/5272* (2013.01); *C02F 1/56* (2013.01); *G01N 15/0227* (2013.01); *G01N 15/06* (2013.01); *G01N 33/1893* (2013.01); *G05B 11/32* (2013.01); *C02F 2001/007* (2013.01); *C02F 2209/001* (2013.01); *C02F 2209/105* (2013.01); *C02F 2209/11* (2013.01); *G01N 2015/0687* (2013.01); *G01N 2015/0693* (2013.01)

(56) References Cited

U.S. PATENT DOCUMENTS

| | | | |
|---|---|---|---|
| 2003/0231309 A1* | 12/2003 | Fulghum, Jr. ...... | G01N 15/0205 356/338 |
| 2009/0098022 A1 | 4/2009 | Tokhtuev et al. | |
| 2011/0060533 A1 | 3/2011 | Jorden et al. | |
| 2013/0161262 A1 | 6/2013 | Henley | |
| 2013/0335731 A1 | 12/2013 | Jorden | |
| 2014/0002662 A1 | 1/2014 | Lewis et al. | |
| 2015/0114094 A1 | 4/2015 | Vähäsalo et al. | |

FOREIGN PATENT DOCUMENTS

| | | |
|---|---|---|
| CN | 1273597 A | 11/2000 |
| CN | 101296870 A | 10/2008 |
| CN | 101432232 A | 5/2009 |
| CN | 102137818 A | 7/2011 |
| CN | 103708590 A | 4/2014 |
| CN | 104245922 A | 12/2014 |
| CN | 104271836 A | 1/2015 |
| CN | 104968609 A | 10/2015 |
| EP | 0240974 A2 | 10/1987 |
| EP | 2248769 A3 | 11/2010 |
| JP | 57119898 A | 7/1982 |
| JP | 01199608 A | 8/1989 |
| JP | 1199608 A | 8/1989 |
| JP | 08-052459 | 2/1996 |
| JP | H0817893 B2 | 2/1996 |
| JP | 1157739 A | 3/1999 |
| JP | 3199897 B2 | 8/2001 |
| WO | 2004052794 A1 | 6/2004 |
| WO | 2004110935 A1 | 12/2004 |
| WO | 2009108223 A3 | 9/2009 |
| WO | 0226638 A1 | 5/2013 |
| WO | 2013061057 A1 | 5/2013 |

OTHER PUBLICATIONS

Anonymous: "Horiba Scientific, a Guidebook to Paricle Size Analysis", California, USA, Jan. 1, 2012, pp. 1-32.
Finnish Search Report dated Oct. 20, 2016.
International Search Report (PCT/ISA/210) dated Jul. 18, 2017, by the Finnish Patent Office as the International Searching Authority for International Application No. PCT/FI2017/050229.
Vasil'ev I G et al., "Instrument for Monitoring Concentration and Size of Microparticles Suspended in High-Purity Transparent Liquids", Measurement Techniques, Consultants, New York, USA, vol. 35, No. 4, Apr. 1, 1992, pp. 507 and 508.
Written Opinion (PCT/ISA/237) dated Jul. 18, 2017, by the Finnish Patent Office as the International Searching Authority for International Application No. PCT/FI2017/050229.
Chinese Office Action for application 201780028406.2 dated Feb. 20, 2021. No Translation provided.

* cited by examiner

Fig. 6a
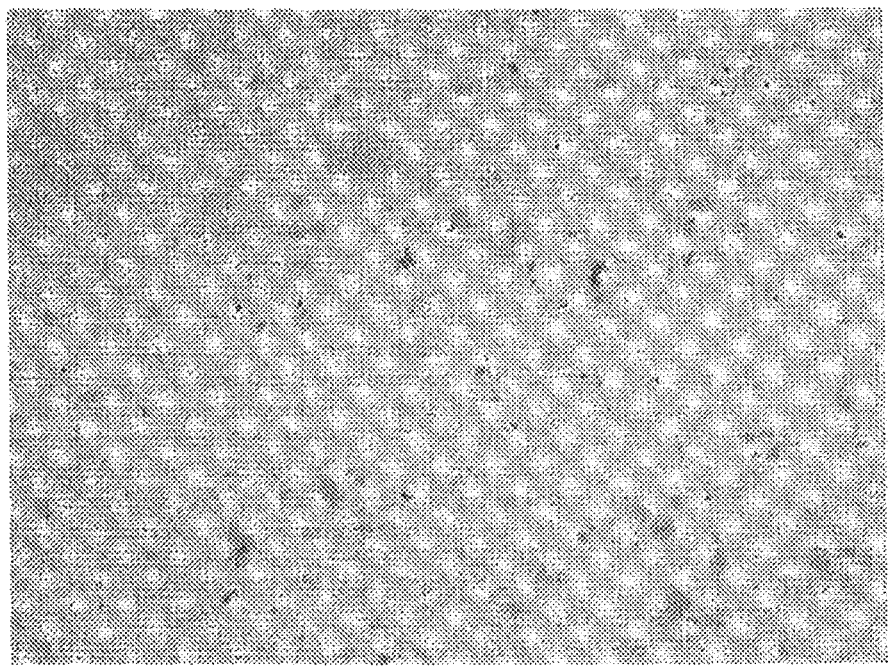
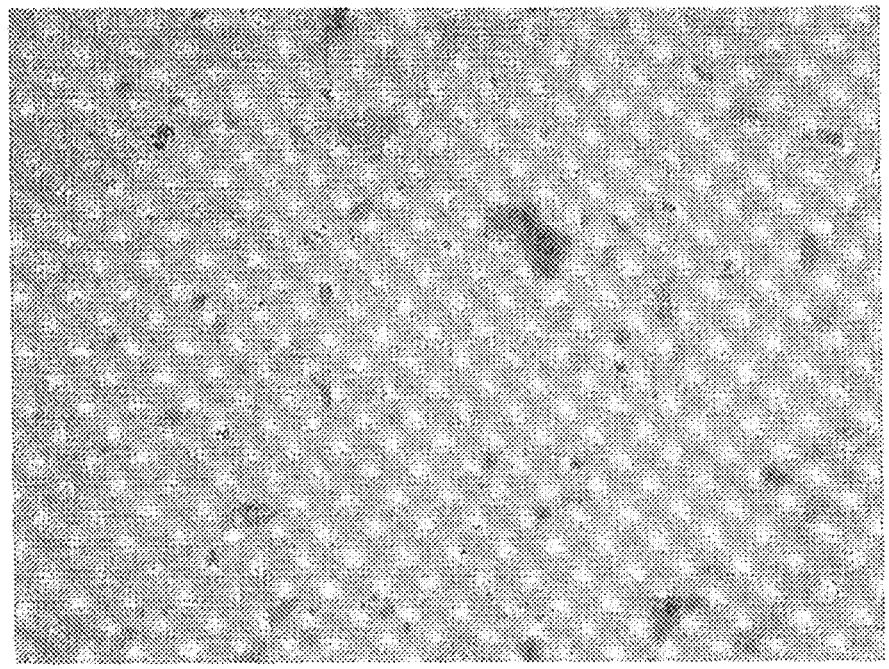
Fig. 6b

Fig. 6c
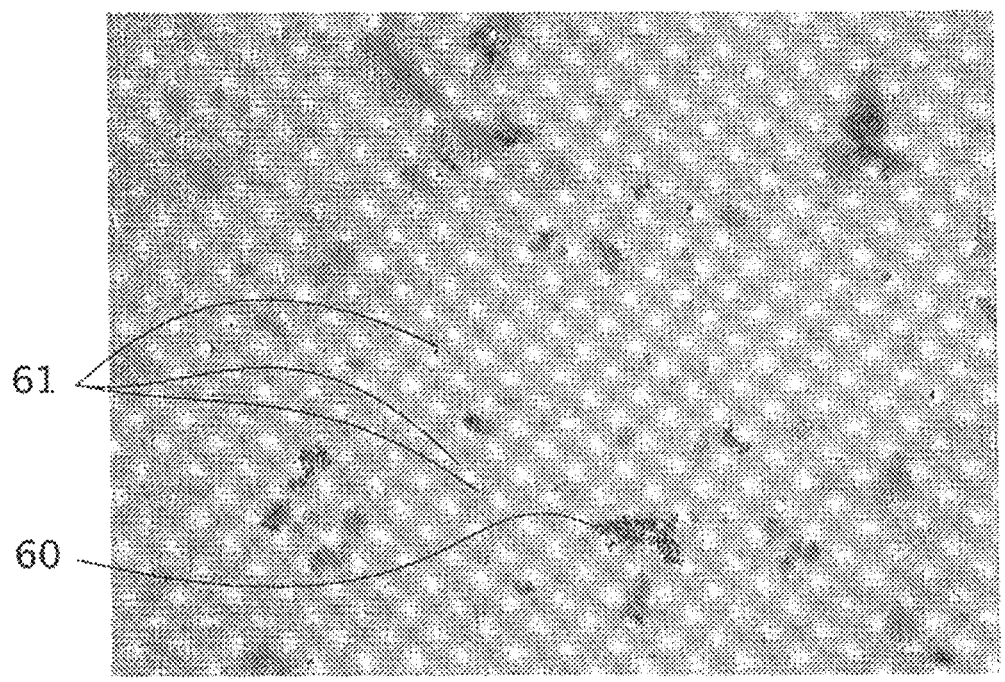
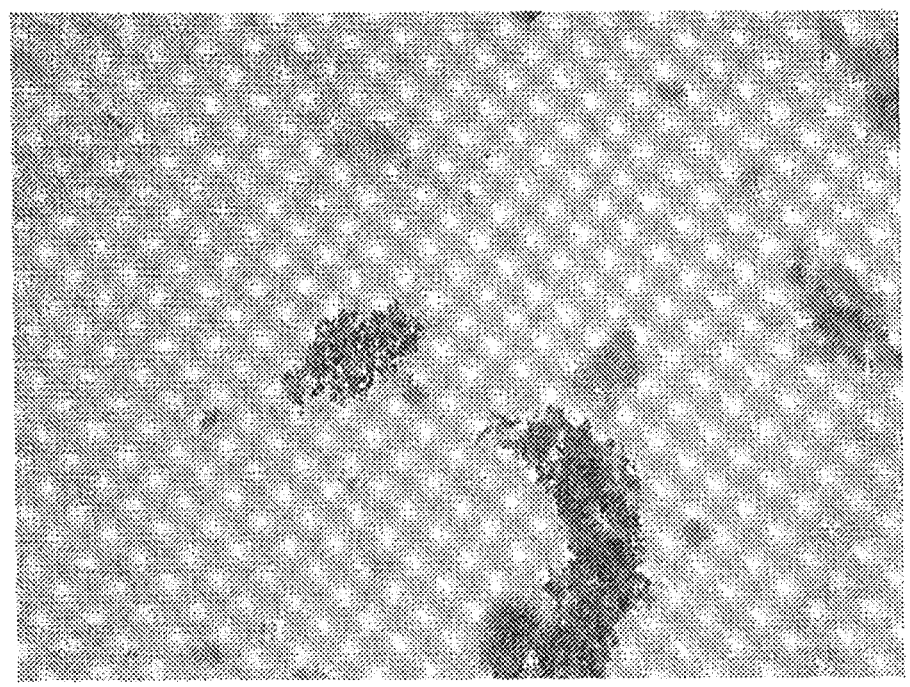
Fig. 6d

METHOD AND SYSTEM FOR OPTIMIZATION OF COAGULATION AND/OR FLOCCULATION IN A WATER TREATMENT PROCESS

FIELD OF THE INVENTION

The present invention relates to water treatment. More specifically, the invention is directed to a method and a system for monitoring and/or optimization of coagulation and/or flocculation in a water treatment process.

BACKGROUND OF THE INVENTION

Effective water treatment requires removal of dissolved compounds and dispersed and suspended solids from the water. This treatment is typically enhanced by chemicals like coagulants and flocculants. Chemicals are added to water stream before separation unit, such as flotation and sedimentation. Usually the conventional measurements based on secondary parameters, such as sedimentation rate or treated water turbidity are used for monitoring the purification results.

On-line control of the coagulant and flocculant dosage is beneficial both economically and ecologically. The on-line control aims at optimizing the chemical dosage while maintaining the high quality of the treated water. The solutions currently available do not provide methods for optimization of coagulation and/or flocculation in a water treatment process.

SUMMARY OF THE INVENTION

It is an object of the present invention to present an improved method and system for monitoring and/or optimization of coagulation and/or flocculation in a water treatment process. According to a first aspect of the invention, the inventive method involves the steps of:
  taking samples from aqueous liquid;
  monitoring the samples with an imaging device to capture visual data of particles dispersed or suspended in said liquid;
  classifying particle types based on said visual data;
  computing a particle size distribution indication for at least one classified particle type;
  comparing said particle size distribution indication to a predetermined particle size distribution value;
  adjusting, at least partially in response to a difference detected in the comparing step, the dosage of at least one coagulation and/or flocculation agent in the water treatment process.

The classification of the particles may in some embodiments be based on shape factors. In some embodiments the classification may be based on the size of the particles. In further embodiments, the classification may be based on color factors of the particles, or any combination of the aforementioned physical properties of the particles. The particle types may comprise one or more of the following: a floc, fiber, fluff, micro-particle, microplastics and any other user defined particle type.

In addition, the adjustment of the dosage of one or more chemicals may additionally be based on measurements from the captured visual data, which may be one or more of the following: water color, particle color, turbidity, particle concentration, micro-particle size and concentration, floc growth rate during flocculation, and floc settling of said liquid flow.

The classification and the dosage adjustment are both possible to carry out with the inventive method and system, which make use of or comprises an imaging device adapted to capture visual data of particles dispersed or suspended in the liquid.

The aqueous liquid to be monitored may be e.g. surface water, ground water, brackish water, salt water, any raw water, wastewater or industrial process water. The aqueous liquid may be flowing to a separation unit, such as flotation, sedimentation, reverse osmosis, nanofiltration, ultrafiltration or a microfiltration process.

The at least one chemical is selected from coagulants and flocculants, preferably selected from water-soluble salts or anionic, nonionic and cationic polyelectrolytes of univalent or multivalent cations, such as sodium, calcium, magnesium, iron, aluminum, natural products such as starch, semi-synthetic polymers such as cationic starch and synthetic polymers such as acrylic polymers, polyamines, polyethylene oxides and allylic polymers, or a mixture thereof.

According to a second aspect of the invention, an inventive system for monitoring and/or optimization of coagulation and/or flocculation in a water treatment process, the system comprising a data processing unit, and functionally connected to said data processing unit:
  means for taking samples from aqueous liquid;
  an imaging device adapted to capture visual data of particles dispersed or suspended in said liquid,
  means for controlling the dosage of at least one coagulation and/or flocculation agent to the water treatment process, wherein
said data processing unit comprising a non-transitory computer readable medium having stored thereon a set of computer executable instructions for causing the data processing unit to carry out the steps of:
  classifying particle types based on said visual data;
  computing a particle size distribution indication for at least one classified particle type;
  comparing said particle size distribution indication to a predetermined particle size distribution value;
  in response to a detected difference between said computed particle size distribution indication and said predetermined particle size distribution value, adjusting the dosage of at least one flocculation and/or coagulation agent for said particles to said aqueous liquid flow.

The present invention offers a multitude of advantages, including detection of particle properties in water treatment processes or particle properties, such as floc properties in a pre-treatment stage of various filtration and membrane processes. With the invention, it is possible to optimize coagulant and/or flocculant dosages, while maintaining a high quality of the treated water.

The various advantageous embodiments of the invention are characterized by what is said in the appended claims.

BRIEF DESCRIPTION OF THE DRAWINGS

Example embodiments of the invention is in the following described in further detail by making reference to the appended drawings, where

FIGS. 6a-6d show visual evidence of the effects in FIG. 5;

DETAILED DESCRIPTION OF EMBODIMENTS

Figure 1:
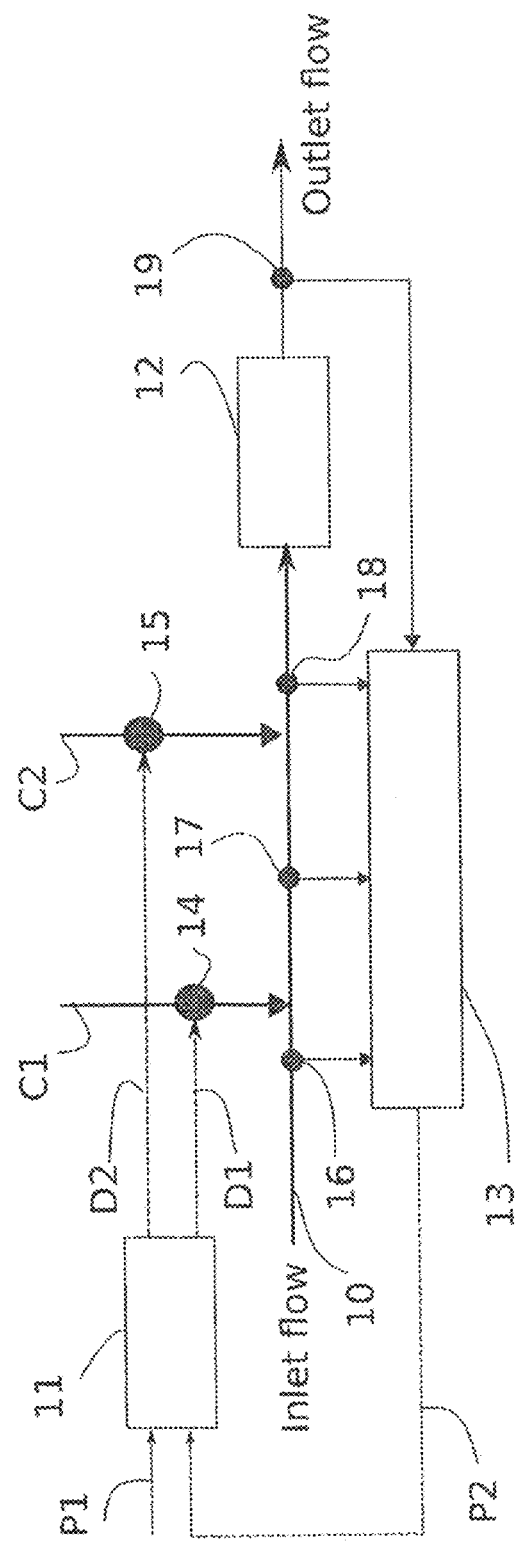
FIG. 1 shows a schematic view of a plant being provided with a particle size and chemical dosing system according to the invention.

FIG. 1 shows a schematic view of a water treatment plant being provided with an image analysis and chemical dosing system according to an embodiment of the invention. The plant consists of a main process stream 10 having an inlet and an outlet flow, as shown. A main component of the plant is a separation unit 12, where flotation, sedimentation, filtration and/or membrane processes are applied to separate the particles from the water flow. Control unit 11 and an image analyzing unit 13 are responsible for water treatment processes involving correct dosage of chemicals C1 and C2, in response to measurements based on image analysis, as will be described in detail below.

Figure 4:
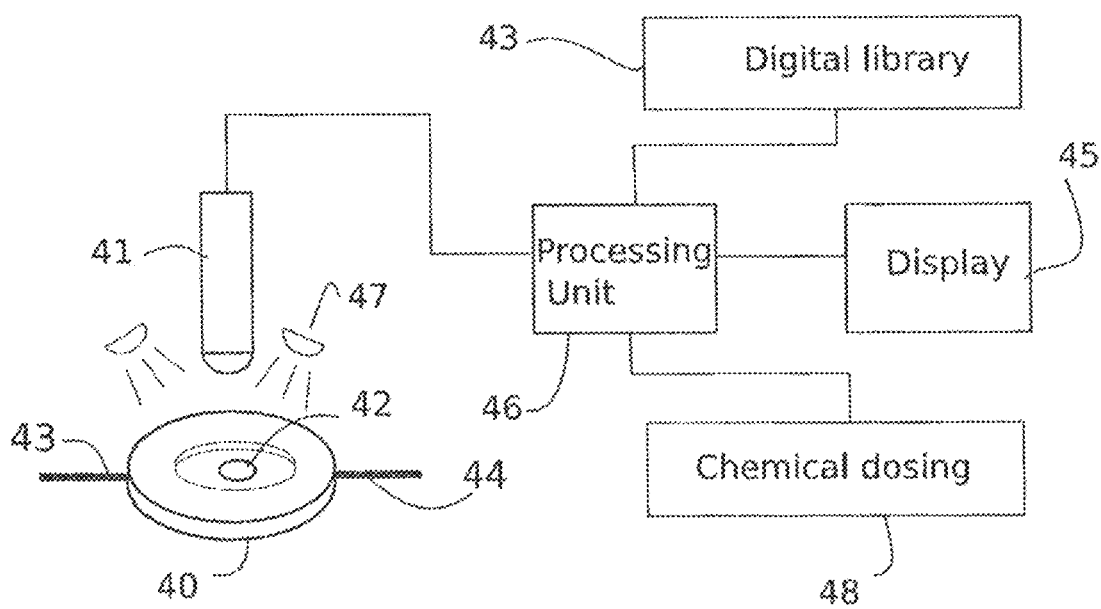
FIG. 4 shows a schematic picture of a monitoring system according to an embodiment of the invention.

Measuring points at 16, 17, 18 and 19 have means such as valves (not shown) for taking samples from different points along the process stream 10 for the image analyzing unit 13, which may contain one or several units of the type shown in FIG. 4. Particle size control chemicals C1 and C2 and other chemicals, if applicable, are added at dosage points 14 and 15 which comprise means for controlling the dosage, such as valves (not shown) remotely controllable by the control unit 11. These points are preferably interleaved between the measuring points 16-18, in order to be able to react to any measurement results indicating a necessity for a chemical dosage adjustment. Dosage adjustments are determined in the control unit 11, based on predefined data P1 stored in a memory (not shown) and which may contain information about target value(s) for particle size distribution, particle concentration, turbidity and/or color of water, and/or reference values of particle size distribution, particle concentration, turbidity and/or color of water in standard samples. Data P1 is compared in the control unit 11 with measured feedback data P2 from the image analyzing unit 13.

The control signals for the valve at point 14 are sent by line (or a wireless channel) D1, and the control signals for the valve at point 15 over channel D2, respectively.

In some embodiments, one chemical C1 is added dosage point 14, and the particle size distribution is measured at measuring point 17. The measured particle size distribution P2 is compared to a predefined particle size distribution value P1. The comparison result is computed and given as feedback to an algorithm in the control unit 11 for computing a corrected dosage of chemical C1, if necessary.

The image analyzing unit 13 may in some embodiments measure the particle concentrations and the particle size distribution for all types of detected particles in the process water, and the turbidity and color of the water. Particle concentrations may be used as dosage criteria for the chemicals C1 and C2 as a complement to the particle size distribution, and the turbidity also correlates with the particle counts, especially for small particles. Color can correlate with the concentration of dissolved organic substances like humus and fulvic acid. In some embodiments, the removal of color is one primary target for the water purification process, whereby an optimal dosage of chemicals may rely both on results of color analysis result and particle size distribution analysis. For example, coagulant chemicals may be dosed based on the color of the water, and flocculant chemicals based on the particle size distribution.

Thus, in some embodiments, one chemical C1 is added dosage point 14, and the particle size distribution is measured of a sample collected at measuring point 17 and the color or turbidity or particle concentration at measuring point 19. The measured values are compared to predefined corresponding values, the comparison results are computed and given as feedback to an algorithm in the control unit 11 for computing a corrected dosage of chemical C1, if necessary.

In some exemplary embodiments, the chemical C1 added to the process stream at dosage point 14 may be a coagulant and the dosage of C1 may then be based on the color of the water sampled at 19 and/or 16. A chemical C2 added to the process stream at dosage point 15 may be a flocculant, and the dosage of chemical C2 may then be based on the particle size distribution sampled at 18.

In some exemplary embodiments, the chemical C1 added to the process stream at 14 may be a coagulant and the dosage of C1 may then be based on the size distribution of small particles sampled at 17. The chemical C2 added to the process stream at 15 may be a flocculant, and the dosage of chemical C2 may then be based on the particle size distribution of flocs sampled at 18. The particle size distribution measured at sampling point 19 then gives an overall view of the effectiveness of both chemicals C1 and C2 and can be used for fine-tuning the dosing control of Chemical C1 and C2.

In another exemplary embodiment, the chemical C1 added to the process stream at 14 may be a coagulant and the dosage of C1 may then be based on the size distribution of small particles sampled at 16. The chemical C2 added to the process stream at 15 may be a flocculant, and the dosage of chemical C2 may then be based on the particle size distribution of flocs sampled at 17. The particle size distribution measured at sampling point 18 then may give an overall view of the effectiveness of both chemicals C1 and C2 and can be used for fine-tuning the chemical dosing.

In other embodiments, the chemicals C1 and C2 may be totally or partially the same chemicals. The sampling points 17 and 18 are then used to further fine-tune the dosages of chemicals C1 and C2.

In many instances, large temperature variations or other natural phenomenon that relate to the time of the year, or exceptional circumstances, may result in that the dosage cannot be optimized based on measurements from one sampling point only.

Measuring the particle size distribution before and after the separation unit 12 at sampling points 18 and 19 respectively, yields of course further and important measurement data which allows for a refinement of the coagulant and flocculant dosage control algorithms applied in the control unit 11.

The chemicals C1 and C2 may be selected from coagulants and flocculants, preferably selected from water-soluble salts or anionic, nonionic and cationic polyelectrolytes of univalent or multivalent cations, such as sodium, calcium, magnesium, iron, aluminum, natural products such as starch, semi-synthetic polymers such as cationic starch and synthetic polymers such as acrylic polymers, polyamines, polyethylene oxides and allylic polymers, or a mixture thereof.

Figure 2:
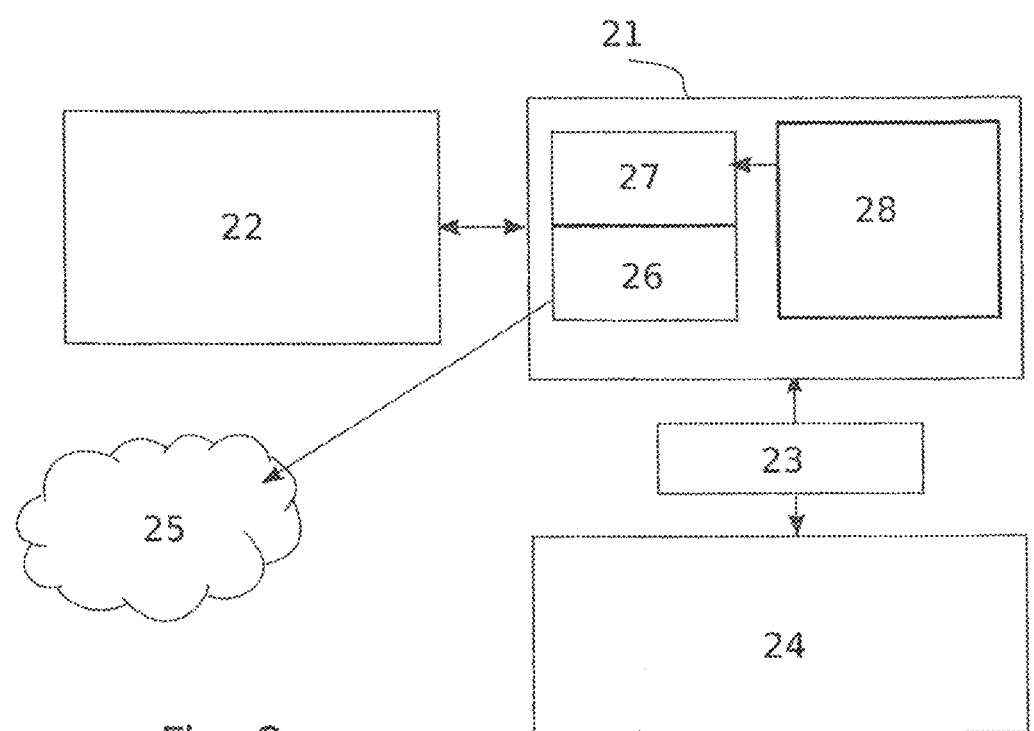
FIG. 2 shows a schematic overview of a data processing unit for a monitoring unit according to an embodiment of the present invention.

FIG. 2 shows a schematic overview of a data processing unit for a monitoring unit according to an embodiment of the present invention. A programmable logic controller (PLC) 21, for example a Siemens S7-1200 PLC is used to control the hardware of the analyzing equipment. An industrial or general-purpose computer 24 runs the analysis software required for the visual data processing and image rendering. Further main components are a touchscreen interface 22, such as a Siemens SIMATIC Human Machine Interface Panel for example, a communication software library 23 and the internet 25.

The communication library 23 may be an Open Data Communications Data Access (OPC DA) client that provide the analysis software running on the computer 24 with synchronous read and write access to the PLC's 21 memory. The analysis software requests a connection from the communication library which then tries to establish the connection to the PLC 21. The connection is then active until the analysis software is closed, and provides access to various PLC memory variables for the analysis software via a multitude of functions.

The PLC program is used to control the hardware of the analyzer. It has a data block 26 used for online data-acquisition via a router that sends the data in the data block to a server on the internet 25. The hardware controller 27 controls e.g. control valves, the camera and a LED lights for illumination.

The PLC 21 also has a data block 28 which can be accessed symbolically and that contains software modules designed for camera and lighting control.

The touchscreen user interface 22 is used to control the inventive system in this embodiment, to configure the connection settings, set the analysis parameters and to visualize the current status of the analyzer.

Figure 3:
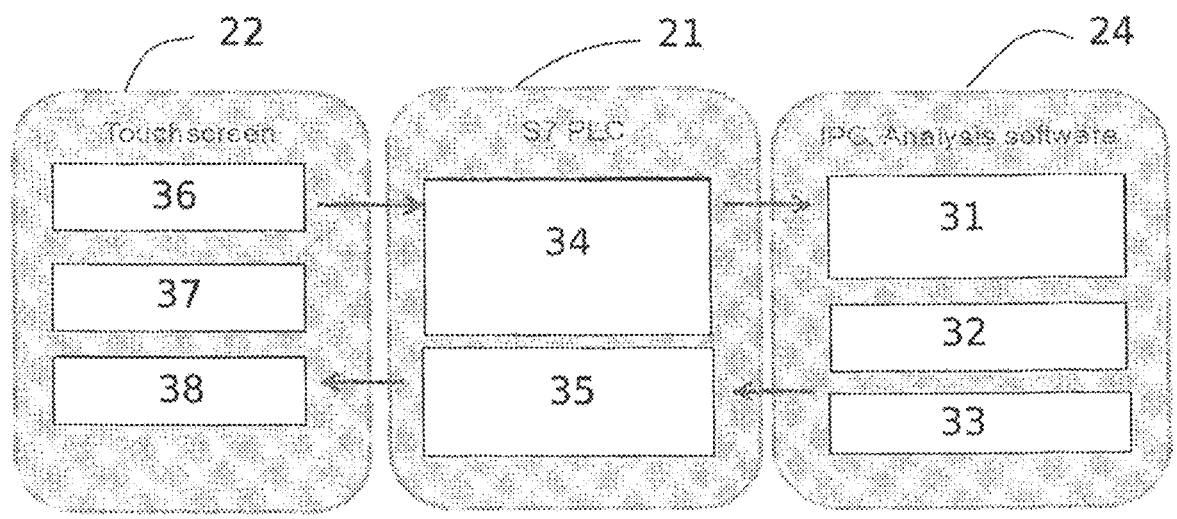
FIG. 3 shows a modular software concept for controlling a processing unit according to an embodiment of the invention.

In FIG. 3 is shown an embodiment of a modular software concept for controlling the data processing unit of FIG. 2. In this embodiment, the touchscreen 22, the PLC 21 and the computer 24 have their own modules. For the computer, modules included may be a module for control of camera and lighting 31, for image analysis and classification 32, and for storing the measurement data 33. The PLC 21 may have multiple automation modules 34 for sampling, sample dilution, washing, parameter setting and dosing control of chemicals. The PLC also need to have a data transfer module 35 to handle the data traffic between the hardware and itself, and the data exchange between all three units 21, 22 and 24. In an embodiment, the operations of PCL can be included in an industrial PC (IPC).

The touchscreen 22 needs software modules for system control 36, timing 37 and result rendering and viewing 38.

Image Capturing

One aspect of the invention is to analyze water quality and solid contents in a sample of water or suspension. With a digital imaging technique developed, it is possible to measure the characteristics of particles such as particle concentration, size distribution and particle shape factors, like roundness and coarseness. The shape properties are computed from the outlines of the objects.

In FIG. 4 is shown a schematic picture of a monitoring system according to an embodiment of the invention. A camera 41 is collecting visual information about the water led to and/or through a cuvette 40 provided with a monitoring window 42. The cuvette 40 may be a flow-through cuvette and provided with a flow input 43 and an output 44. The water sample is pumped to a flow-through cuvette utilizing a pump (not shown) or the original pressure in the process line. A short inlet pipe 43 from any sampling point of FIG. 1 to the imaging system provides a short time delay between the measurement results and the actual state of the flocculation. Thus, in this embodiment of the invention, the cuvette with its input feed flow constitutes the means for taking samples out of the aqueous process liquid.

The camera 41 collects particle information from the water 42. Illumination is provided by lamps 47 arranged in this exemplary embodiment on the same side of the cuvette 40 as camera 41. The lighting fixture 47 may for example consist of LED lamps or arrays, lasers, Xenon lights or halogen lights. The light may be constant or intermittently flashing (strobe light). The used light may also be of any desired color, in order to best bring the form and features visible to the camera. In other embodiments, backlight may be provided, i.e. the illumination is provided at the opposite side of the cuvette as the camera. In some embodiments, the cuvette may be illuminated from more than one direction.

Data processing unit 46, which is understood to comprise the functionalities of the computer 24 and the PLC 21 of FIG. 2, analyzes the collected visual data from the water 42 and classifies the particles based on information obtained from the visual data and compares it with stored information in a digital library 43. Particularly the particle size distribution is compared to a predetermined optimum particle size distribution value.

Finally it may compute particle size and amount characteristics, which are stored and displayed on display 45, corresponding to the touchscreen 22 of FIG. 2, and/or sent as a control signal to a chemical dosing device 48, which may add or reduce the amount of flocculation control chemicals.

According to an embodiment, on-line analysis may be carried out from water that flows through a cuvette 40. In more detail, the water flow may be monitored with a color CCD camera equipped with a high-magnification objective achieving a micrometer resolution, for example. Pulsed, high-power LED lights are preferably utilized to illuminate the studied objects in the water flow. Images of the flow are then analyzed at the speed of several frames per second. Such measurement provides statistical, time-dependent information on water turbidity and color, particle concentration, size of particles, color of particles, shape of particles and velocity of particles.

Water may flow inside the cuvette in a channel with a height of 3 mm and width of 20 mm, for example. In some embodiments, the cuvette may be positioned in a substantially vertical direction to allow for a substantially vertical flow direction. In some embodiments, the flow direction is preferably from bottom to top to avoid air pockets and channeling of water. The channel height is preferably adjustable. The water flow rate will typically slow down significantly, when entering the cuvette from the pipe. At 60 $cm^3/s$ flow rate, the flow velocity is about 1 m/s. In case of fragile flocs, the flow velocity may be kept lower, as porous flocs may otherwise break up during the sampling. A suitable flow velocity is 0.1 m/s or lower, which corresponds to a flow rate of 6 $cm^3/s$.

The task of the imaging device is in the present invention to capture pictures of water stream and to send the data to a computer which is running an analysis software. The imaging device that can be used in the present invention may consist of a color CCD camera equipped with a high-magnification lens, for example. The cuvette may be viewed with the camera from a 40 mm working distance.

One example of such an imaging device is the ImperX™ BobCat color camera with an Ethernet connection and a Sony® ICX-285 CCD sensor. Such a sensor may provide 14-bit images at maximum of 24 frames per second with a 1392×1040 pixel resolution. The recorded images may be stored as BMP-files.

Different particles may require different camera sensors. In any image capturing, it is clear to one skilled in the art to apply camera sensors with e.g. appropriate pixel resolution, S/N ratio and sensitivity to various wavelengths of light, to obtain the best results.

The imaging system utilizes pulsed, high-power LED lights to illuminate the studied objects in the water samples. For example, a diode laser by Cavilux® is proven to provide enough light power to the measurement volume. In an exemplary setup, three LED lights are in the front of and one LED light is behind the cuvette, which may be controlled separately to optimize the image quality. Back-light illumination of dispersed or suspended solids helps to obtain the silhouettes of particles.

The color spectrum of the illumination source of course affects the colors reflected by the objects, why the LED lights preferably are easily changeable for optimum reflection and camera detection. For example, the illumination light spectrum may use white LED light for general measuring conditions. White LED lights have a sharp peak at blue wavelengths (460 nm) and a local minimum between the blue and green wavelengths, around 500 nm. Ultraviolet light (UV) may be used for better image resolution of micro-particles.

The inventive system and method utilizing visual data captured with a flow-through imaging cuvette or similar device can be used to provide different kinds of measurements. Measurements include characterization of dispersed or suspended solids, e.g. flocs (e.g. porous flocs using back-light illumination) in a flowing water sample, water turbidity measurement, water color measurement, measurements of micro-particle size and concentration, measurements of floc growth rate during flocculation (by circulating flocs through the cuvette) and floc settling velocity in stagnant water, as well as water and particle color measurements.

If the water to be analyzed has a too high particle concentration, the samples can be diluted. Dilution can be performed automatically by programming the PLC 21 to perform such a routine, for example. The dilution factor can be constant or it can be changed according to the measured image brightness, for example.

Image Analysis

The inventive imaging system will produce high-magnification, digital images of the micro-scale objects dispersed or suspended in an aqueous flow. Manual analysis of such images would be exhaustive and time consuming. Therefore, an automatic and robust image analysis method is needed to detect and analyze the various objects in the images in order to obtain acceptable and comparable results that reveal the main characteristics of the particles dispersed or suspended in the water sample. Each required step will be presented in detail in the section to follow. The analysis is mainly taking place in the processing unit 46 of FIG. 4.

Filtering & Greyscale Correction

Image filtering is utilized to remove noise, to even out a difference in the background, to highlight the regions of focused objects, and to compute higher order moments of image greyscales such as local greyscale gradient values and their direction. The image may first be equalized by subtracting and then dividing a low-pass filtered image generated with a Gaussian multiresolution pyramid. This approach effectively evens the image background and removes large blurred objects from the image.

A Laplacian image, which is the second derivative of image greyscales, is computed from the equalized image and the absolute Laplace transform value is computed. Laplacian image highlights the regions of the greatest greyscale variance, for example objects with sharp texture, small objects and sharp outlines. Focus discrimination may be realized on the Laplacian image with a user-defined focus threshold. For example, only objects whose projected area has more focused pixels relative to the total area than the user-specified focus ratio of 7% are recognized as valid.

Greyscale gradient images and gradient direction angle images are computed from the equalized image. This information is important and may be used in a multitude of computations. Basically the greyscale determines the object outline. The gradient image, which is the hypotenuse of the greyscale gradients in the x- and y-directions, may then be multiplied with a user-defined gradient-multiplier value, before superimposing it on a high-pass filtered image.

Image segmentation methods try to automatically recognize focused objects in an image, and to compute their projective areas and silhouettes, i.e. their outlines. Image segmentation is usually carried out in steps, in order to be able to recognize different types of objects. Dark regions may be recognized from an equalized image by using a greyscale percentile threshold. Such a greyscale percentile may be a user-specified value, determined from a cumulative greyscale histogram of the equalized image. The greyscale percentile threshold determines the contrast threshold value applied for rejecting false particle detections from images of clean water. A binary image of an object may thus be obtained by segmenting the image with the user-specified contrast threshold, and by superimposing on it the dark regions.

A sample cell or cuvette background image may be computed as the mean image of the previous 10 images. Stagnant objects are segmented from the background image using the above mentioned greyscale percentile threshold. The total area of background objects per total image area represents a current fouling value. The detected stagnant objects may then be digitally masked out from further analysis of the current image.

Particle Characterization

A binary image of an object may be processed with morphological operations to determine for example its actual boundaries and the shape of the object. Aspect ratio, roundness, and coarseness are usually interesting input parameters for further analysis and object classification of the object. First, the projective area of each object is imaged by the camera. The diameter d of an object may be defined based on the object's projective area A as:

$$d = 2 \cdot \sqrt{\frac{A}{\pi}} \quad (1)$$

Principal axes and aspect ratio are computed from the particle image by using a principal component analysis (PCA) algorithm. The algorithm returns the major and minor axes of the particle and their orientation angle. The aspect ratio is the ratio between the major and minor axes. The aspect ratio of a circle is thus=1.

Roundness of an object determines how circular the particle is. Round objects have 100% roundness and as the roundness percentage decreases with increasing the complexity of the particle shape, it shows how much a particle outline shape deviates from a circle. Roundness R may be computed as:

$$R = \left(1 - \frac{\sqrt{\frac{\sum_i^N (r_i - r)^2}{N-1}}}{r}\right) \cdot 100\% \quad (2)$$

where r is the object radius and $r_i = \sqrt{(x_i-x_c)^2+(y_i-y_c)^2}$ are the distances from outline pixels $(x_i,y_i)$ to the center point of the object $(x_c,y_c)$. Normalization is obtained by dividing the standard deviation of radii with the object radius, which produces a scale that is inversely proportional to changes in sizes, making the comparison of shapes easier.

Coarseness of an object is computed as the sum of discrete curvatures along the perimeter divided by the length of the outline. Discrete curvature values are computed as the difference between greyscale gradient direction angles of neighboring outline pixels. Only the discrete curvatures of spikes (i.e. sharp turns) are relevant in a coarseness computation. For example, a spike may be determined to exist when the direction angle changes more than 0.9 rad in a positive direction, or less than 0.5 rad in a negative direction. The outline is studied through directional angles from $-\pi$ to $\pi$. The coarseness value may be normalized with a factor $\pi \times d_{max}$ (maximum dimension of the particle), which is the outline length for a circular particle. Bubbles, droplets and other blobs then obtain low coarseness values, whereas fibers and flocs have higher coarseness values.

The texture of a particle image is important for cognitive recognition. The particle texture may be modeled by studying the brightness (i.e. greyscale) profile from particle center point to particle outline, covering the full particle area. The standard deviation of particle's brightness values may also be computed. The mean brightness value is used to discriminate particles to bright and dark particle classes. Thus bright and thin fibrous objects may be classified as fluff, for example.

Particle Classification

Particle classification may generally speaking rely on a hypercube approach, which means that a particle or object is classified to a particle class when particle's every property remains between the discrete minimum and maximum limits specified for the class. Classification limits can obviously be modified in a configurations-file of the computer running the classification algorithm(s).

Each detected particle is strived to be classified to one specific particle type or class. Such particle types or classes may be flocs, fibers, fluff (i.e. small, bright fibrous particles), micro-particles, microplastics and other particles.

A micro-particle is a particle smaller than 20 μm in diameter, for example. Various parameter values of the particle image may be recorded, if of interest. When an object is not a micro-particle, its shape properties etc. are computed as described below.

It is also possible to obtain the particle length and width. Computation is based on arranged outline vectors consisting of the x,y-coordinates of each outline pixel and the greyscale gradient direction value $[-\pi, \pi]$ at each outline pixel. The matching point at the opposite side of the particle image is the nearest pixel that have the opposite greyscale gradient direction values. The direction values between the opposite outline pixels may also be compared. The distance between the opposite pixels corresponds to the local width of a particles. Overall particle width is computed as the mean of local widths. Overall particle length is computed as the length of the particle outline divided by two.

For example, fibers have low roundness values (<38) and low coarseness values (<60). If particle's aspect ratio is larger than 5, the particle is then classified as fiber.

For example, a particle may be classified as wood fiber if its roundness and coarseness values fit into predetermined classification limits for a fiber. Then a specific analysis may be carried out to compute the fiber length and width and aspect ratio. If the aspect ratio is larger a predetermined ratio limit for a fiber, the classification as a fiber is confirmed.

If a particle is not classified as a fiber, a principal component analysis may be carried out to get the major and minor axes of the particle image and their aspect ratio. The particle is then classified as floc, if its roundness and coarseness values fit into predetermined classification limits for a floc. Flocs are distinguished based on their high coarseness value, which may set to exceed 33, for example. Special care must be taken when analyzing samples with porous flocs. Generally, the flow velocity should not exceed 0.1 m/s, in order to avoid floc breakage. Porous flocs consist of fragile structures that may break at the slightest shear force induced by an attempt to transfer them from one vessel to another. There is thus no optimal value for the sampling flow rate, but the value depends on the floc weight and porosity.

A particle may be classified as fluff, if it is brighter than a brightness threshold and fulfills other predetermined size criteria for fluff.

Other particles may be classified as "others". Alternatively, a set of limits and rules are set for desired particles in a similar way as for the basic particle classes described above, to be able to monitor the occurrence of such particles individually.

Figure 5:
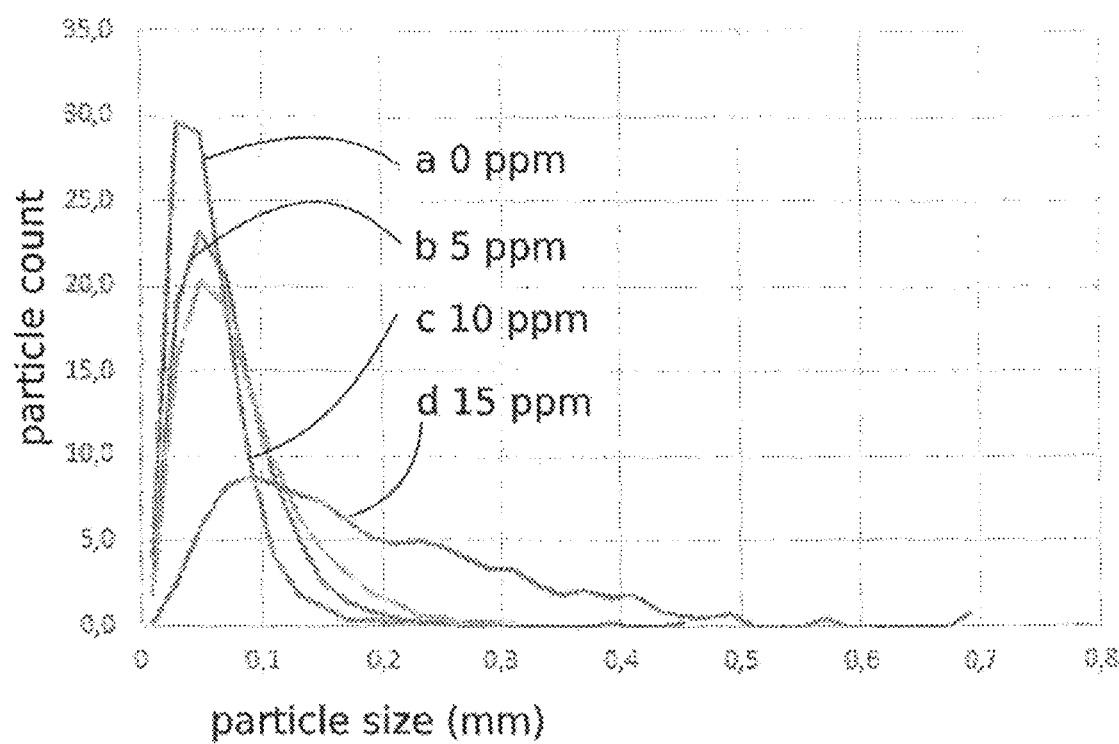
FIG. 5 show the effect of flocculant chemicals on particles in raw process water.

FIG. 5 shows the effect of flocculant chemicals on particles in raw process water. In the figure is clearly shown the effect of coagulant chemicals on particle size (x-axis) and particle count (y-axis). Graph "a" represents particle size distribution for a water stream without any coagulant chemicals. Graphs b-d represents particle size distributions for water streams containing 5, 10 and 15 ppm of coagulant chemicals, respectively.

A data set including particle sizes and corresponding particle counts is a way to obtain a particle size distribution. A particle size distribution value may also be based on any mathematical model derived from such a data set comprising particle sizes and corresponding particle counts. A particle size distribution or any statistical value calculated from the particle size distribution may be used as a particle size distribution value. The statistical value characterizing the particle size distribution may be e.g. skewedness, kurtosis, quartiles, median and mode.

FIGS. 6a-6d show images from raw waste water of a paper mill, with corresponding amounts of coagulant chemicals as in FIG. 5. Untreated water are pictured in FIG. 6a, while FIGS. 6b-6d show the effect of coagulant chemicals in concentration s of 5, 10 and 15 ppm, respectively.

As can be seen from FIGS. 5 and 6a-6d, untreated water contain a lot of small particles. The particle size distribution changes with the amount of coagulant chemicals added, and so-called flocs are formed, which are easier to remove in a separation unit. By comparing the particle size distribution indication to a predetermined optimum particle size distribution value, it is possible to optimize the chemical dosage in order to reduce the amount of small particles to a minimum. Small particles are the most difficult ones to remove with sedimentation or flotation techniques. In FIG. 6c is shown by way of example a typical floc particle 60 and some microparticles 61.

Water Quality Assessment

Embodiments of the invention can be utilized in multiple different kinds of measurements, for example:
- Measurement and characterization of dispersed or suspended solids in flowing water sample, such as size, shape, count, color and type
- Water turbidity measurement, particle concentration measurement
- Measurement of micro-particle size and concentration,
- Measurement of floc growth rate during flocculation, circulating flocs through the cuvette,
- Floc settling velocity measurement in stagnant water,
- Measurement of porous flocs with telecentric back-light illumination,
- Water color measurement The volume of a particle may be estimated from its projected-area diameter. The volume is approximated assuming that the particle is a sphere with a diameter equal to the projected-area diameter. The volumes of all valid particles are summed up and the sum is divided with the measuring volume i.e. the camera's field of view multiplied by the depth of the viewed field, which may be 0.15 mm, for example. In order to get the solids concentration in ppm, the concentration is multiplied with $10^6$.

The water turbidity is computed using the mean value of gradient image and mean greyscale value. Water turbidity is scaled with camera sensitivity value and dilution factor to get the true turbidity estimate of the process water.

Both particle color and water color can be measured with a color camera. Results can be stored as RGB-values, for an example.

Flocculation Control

According to an important aspect of the invention, the dosage of flocculation and/or coagulation agents in a monitored aqueous liquid flow is adjusted in response to a detected difference between a computed particle size distribution value and a predetermined optimum particle size distribution value.

Figure 7A:
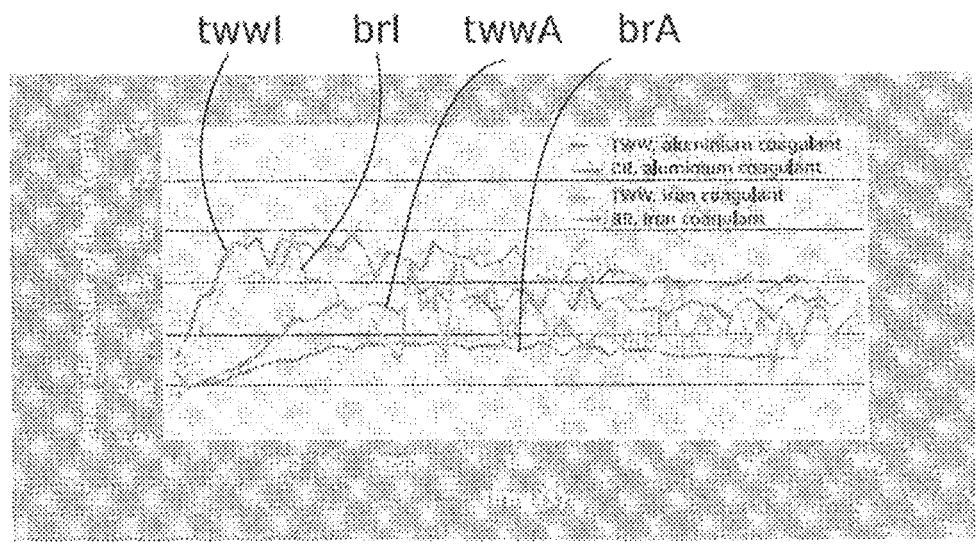
FIGS. 7a and 7b show development of floc size and count as a function of time in a water treatment process conducted according to the invention.
Figure 7B:
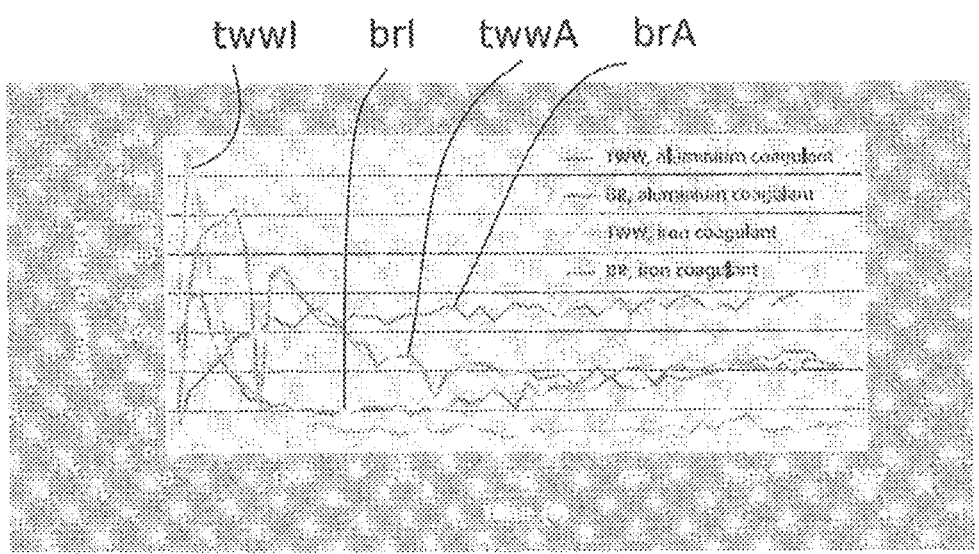

The inventive floc monitoring system has been tested with different dosages and types of coagulants, among others to treated waste water (tww) and low-saline (brackish) sea water (br) using iron and aluminum salt coagulants. FIG. 7a show the development of floc size and FIG. 7b the development of floc count as a function of time during 10 minutes for these two water types and coagulants.

In the figures, online imaging started 60 seconds after iron or aluminum salt addition. For the iron coagulant (twwI and brI), floc growth was faster than for aluminum coagulant (twwA and brA). The results show that iron coagulant could be more suitable than aluminum coagulant in microfiltration (MF) and ultrafiltration (UF) pretreatment units. In general, 10 minutes (600 seconds) of contact time is enough for the floc count and size to stabilize.

The results of image analysis clearly shows that the iron-based coagulant formed larger flocs while the aluminum-based coagulant formed smaller but more numerous ones. During 1 minute of flocculation the mean size for iron-treated flocs reached a value of 80 μm but for aluminum-treated flocs the size was about 50 μm.

In practice, with the aid of the inventive system and method, floc growth can be monitored online during flocculation. The inventive system gives valuable information of floc properties and reaction times optimum control for a water processing plant pretreatment stage.

FIGS. 8, 9, 10, 11 and 12 illustrates utilization of particle size distribution for adjusting dosing of chemicals according to exemplary embodiments.

Figure 8:
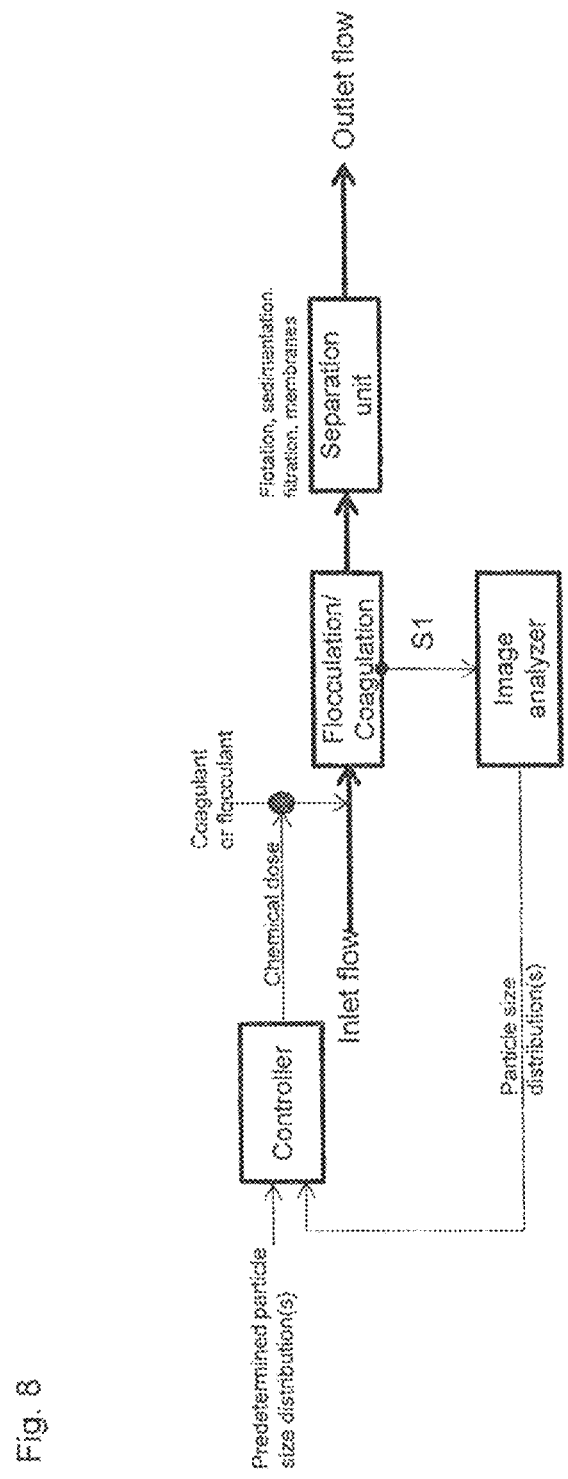
FIGS. 8, 9, 10, 11 and 12 illustrate the utilization of particle size distribution for adjusting dosing of chemicals according to an embodiment.

FIG. 8 illustrates adjusting dosing of one chemical and having one sampling and/or measuring point. The controller may be e.g. a PI type controller. A control algorithm may be any mathematic equation that outputs a chemical dose according to a difference between a measured size distribution and a predetermined size distribution. The particle size distribution used for the adjusting in the controller may be the particle size distribution of all particles (all detected particles), flocs, small particles (microparticles), and/or of any other particle type. More than one particle size distributions may be used for adjusting the chemical dose. Depending of the particle size distribution, the type of the chemical may be selected. For example, if the water contains a lot of small particles (microparticles), a short chain polymer with high charge density may be used. If the water contains a lot of large particles, a polymer with a long polymer chain may be used. Based on the size distribution of flocs and/or the microparticle count it may be decided which type of chemical is to be used, e.g. a short or long chain polymer and/or a polymer charge.

In an embodiment, following particle types may be classified from visual data: flocs, small particles (microparticles). The particle size distribution is computed for flocs, and a particle count is computed for microparticles. These values are compared to predefined target values. According to a difference between the computed values and target values, the chemical dose(s) are adjusted. Optionally, water color is computed from the visual data, and the computed water color is compared to a predefined value. Water color depends on compounds dissolved in the water. Thus the intensity of a specific color is an indication of the concentration of dissolved compounds (the color is preferably brownish), and the chemical doses are adjusted according to a difference between a computed color intensity and a target value of color intensity.

In FIG. 8, the sampling point may be after chemical addition but before the separation unit. In FIG. 8, the sampling point may also be after the separation unit or before chemical addition.

Figure 9:
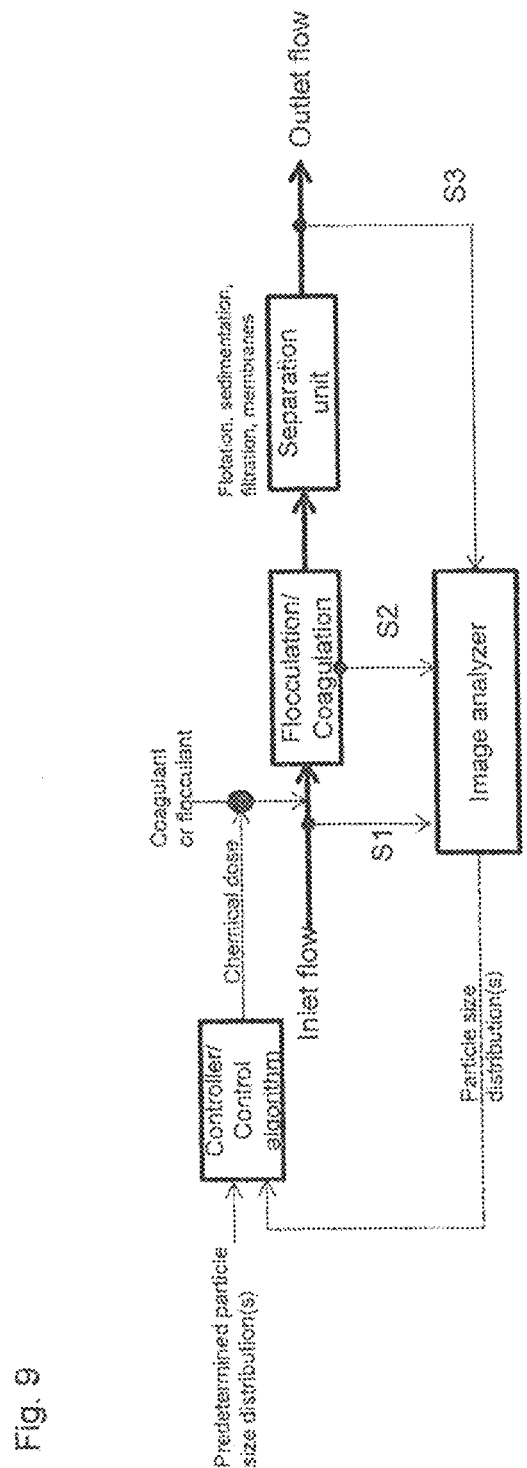

FIG. 9 illustrates adjusting dosing of one chemical and having at least two sampling points S1, S2, S3.

In FIG. 9, the at least two sampling points S1-S3 may be before chemical addition S1 and from the flocculated sample S2, wherein the particle size distribution (and optionally the particle count of microparticles) from the inlet flow may be used for adjusting the level of chemical dose (especially when the quality of incoming water changes a lot), wherein fine tuning of the chemical addition may be done by using the particle size distribution obtained from the flocculated sample S2.

Water color may be measured at S1, wherein it is possible to detect the amount of dissolved compounds which may be used for adjusting the level of chemical dose, wherein fine tuning of the chemical addition may be done by using the particle size distribution (and optionally the particle count of microparticles) obtained from the flocculated sample S2.

Alternatively, in FIG. 9, the at least two sampling points S1-S3 may be from the flocculated sample S2 and after pretreatment S3, wherein both distributions (and optionally the particle count of microparticles) may be used for adjusting the chemical dose according to the control algorithm.

Particle size distribution may be measured at S2, wherein the chemical addition may be adjusted by using the particle size distribution (and optionally the particle count of microparticles) obtained from the flocculated sample S2 and the water color measured at S3.

In another alternative, the at least two sampling points S1-S3 may be before the chemical addition S1 and after the separation unit S3, wherein both sampling points have their own predetermined particle size distribution, wherein the measured size distribution from the inlet and outlet may also be compared (particle reduction for each size). This information may be an input value for the control algorithm.

Three flows S1, S2, S3 may be measured, wherein color is measured from S1 and S3, and particle size distribution (and optionally the particle count of microparticles) is measured from S2. Color and particle size distribution and optionally the particle count of microparticles may be used to adjust the flocculant or coagulant dose.

Figure 10:
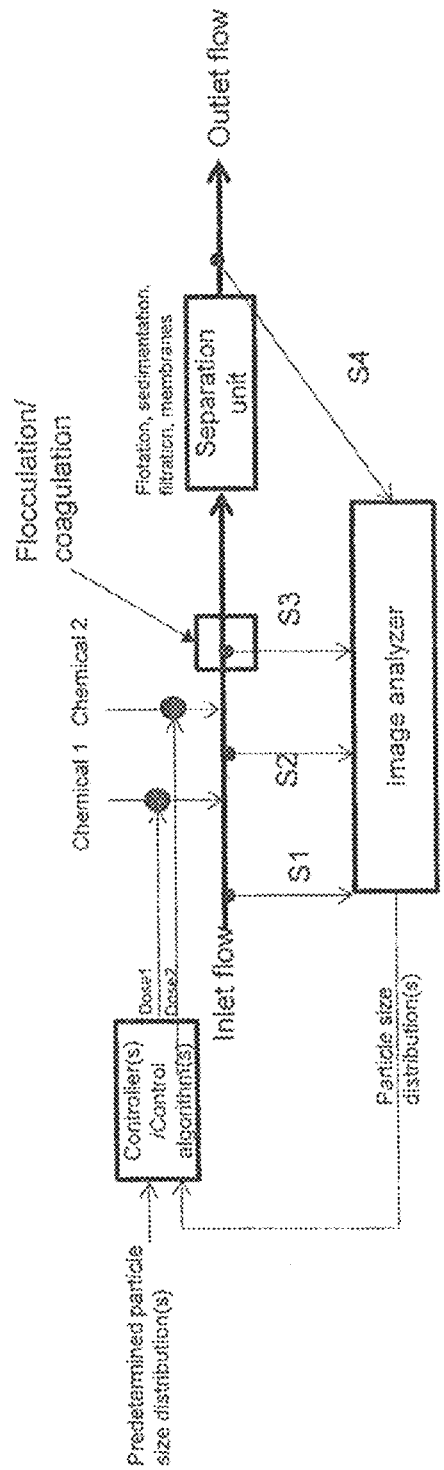

FIG. 10 illustrates adjusting dosing of two or more chemicals, and having at least one sampling point S1-S4. In FIG. 10, chemical 1 may be a coagulant, wherein e.g. the particle size distribution of small particles may be utilized for adjusting the coagulant dose. Chemical 2 may be a flocculant, wherein e.g. the particle size distribution of flocs may be used for adjusting the flocculant dose.

For example, the floc distribution and the microparticle count may be measured from S3, and compared to predefined values, wherein based on the comparing the dosing of chemical 2 (e.g. flocculant) may be adjusted. Further, the particle size distribution may be measured from S1, and compared to a predetermined particle size distribution, wherein based on the comparing the dosing of chemical 1 may be adjusted.

Figure 11:
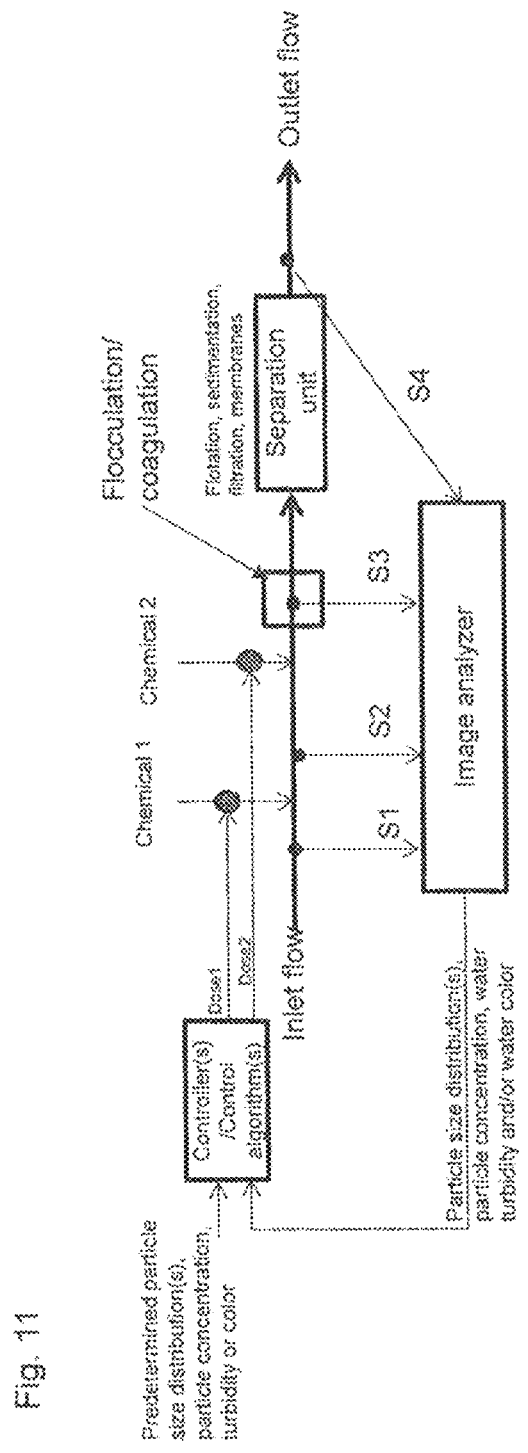

FIG. 11 illustrates adjusting dosing of two or more chemicals, and having at least one sampling point S1-S4. In FIG. 11, particle concentrations (for all detected particles and/or for each particle type) are measured in an image analyzer. The information on particle concentrations may be utilized for adjusting the chemical doses with or without the particle size distribution. The image analyzer may also be configured to measure the turbidity of the water and/or the color of the water. Water color may correlate with the concentration of dissolved organic substances like humus and fulvic acid. The color removal may a main criteria in purification of water, wherein the color may be used for adjusting the chemical dose without and with particle size distribution. Reduction of the color between inlet S1 and outlet S4 may also be measured and used for adjusting chemical dosing. Turbidity correlates with the particle counts, especially the number of small particles. The information on turbidity may be utilized for adjusting the chemical doses with or without the particle size distribution.

For example, the particle size distribution may be measured from S3 and S4, i.e. before and after the separation unit, wherein the measured distributions may be compared to the predetermined size distributions and the flocculant dose may be adjusted accordingly. Water color may be measured at least from the outlet flow S4, and the coagulant dose may be adjusted according to the measured water color.

The particle size distribution of flocs and the count of microparticles may be measured from S3, for example, wherein the measured distribution and particle count may be compared to the predetermined size distributions and particle count, and the flocculant dose may be adjusted accordingly. Water color may be measured from the inlet flow S1, and the coagulant dose may be adjusted according to the measured water color.

Figure 12:
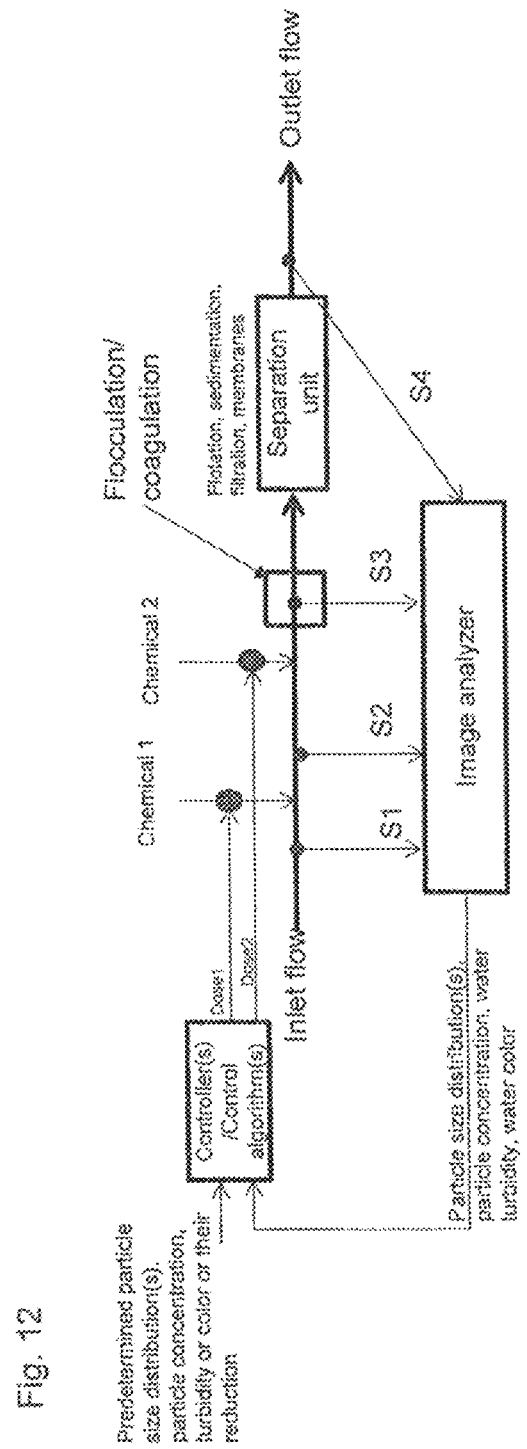

FIG. 12 illustrates adjusting dosing of two or more chemicals, and having at least two sampling points S1-S4. In FIG. 12, an image analyser is configured to measure particle concentrations (for all detected particles and/or for each particle type). The measured concentration information may also be utilized for adjusting the chemical doses with or without particle size distribution. The image analyzer may also be configured to measure the turbidity and color of the water. Water color may correlate with the concentration of dissolved organic substances like humus and fulvic acid. The color removal may be a main criteria in purification of water, wherein the color may be used for adjusting the chemical dose without and with the particle size distribution. Reduction of the color between the inlet and outlet may also be measured and used for adjusting chemical dosing. Turbidity correlates with the particle counts, especially the number of small particles. Turbidity may be used for control purposes, wherein turbidity may be utilized for adjusting the chemical doses with or without particle size distribution. Reduction for the particle size distribution, color, turbidity, particle concentration, specific particle types, specific particle size (size ranges) may also be measured and used for adjusting the chemical dose(s).

An embodiment comprises computing a particle size distribution indication for flocs, and comparing the particle size distribution indication for flocs to a predetermined particle size distribution value.

An embodiment comprises computing a particle count for microparticles, and comparing said particle count for microparticles to a predetermined particle count value.

In an embodiment, the computing of the particle count for the microparticles (small particles) comprises computing the particle count for particles having a particle size of 0.1 to 500 µm, preferably 0.1 to 100 µm, more preferably 0.1 to 20 µm, most preferably 1 to 20 µm.

An embodiment comprises monitoring the samples with the imaging device to capture visual data of compounds dissolved in the liquid.

An embodiment comprises computing water color of the sample based on the visual data captured by the imaging device, and comparing the computed water color to a predetermined water color value.

An embodiment comprises computing a particle size distribution indication for at least one of fiber, fluff, microparticle, microplastics, and any other user defined particle type, and comparing said particle size distribution indication to a predetermined particle size distribution value.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A computerized method for monitoring and/or optimization of coagulation and/or flocculation in a water treatment process, the method comprising:
    taking samples from an aqueous liquid;
    monitoring the samples with an imaging device to capture visual data of particles dispersed or suspended in said liquid;
    classifying particle types based on said visual data;
    computing a particle size distribution indication for at least one classified particle type; and
    comparing said particle size distribution indication to a predetermined particle size distribution value;
    wherein the method comprises at least one of:
        a) computing a particle size distribution indication for flocs, and comparing the particle size distribution indication for flocs to a predetermined particle size distribution value;
        b) computing a particle count for microparticles, and comparing said particle count for microparticles to a predetermined particle count value; or
        c) monitoring the samples with the imaging device to capture visual data of compounds dissolved in the liquid, computing water color of the samples based on the visual data, and comparing the computed water color to a predetermined water color value;
    wherein the method further comprises:
        adjusting, at least partially in response to a difference detected in any one or combination of the comparing steps, a dosage of at least one coagulation and/or flocculation agent in the water treatment process to optimize the coagulation and/or flocculation of the particles dispersed or suspended in the liquid.

2. The method according to claim 1, wherein the computing of the particle count for the microparticles comprises:
    computing the particle count for particles having a particle size of 0.1 to 500 µm.

3. The method according to claim 1, wherein the method comprises:
    computing a particle size distribution indication for at least one of fiber, fluff, micro-particle, or microplastics; and
    comparing said particle size distribution indication to a predetermined particle size distribution value.

4. The method according to claim 1, wherein classifying of the particles is done based on shape factors and/or the size of said particles.

5. The method according to claim 1, wherein classifying of the particles is done based on color factors of said particles.

6. The method according to claim 1, wherein said particle types comprise one or more of the following:
    a floc, fiber, fluff, micro-particle, or microplastics.

7. The method according to claim 1, wherein adjusting of the dosage of at least one chemical to the water treatment process is additionally done based on a measurement from captured visual data, the measurement comprising one or more of the following:
    water color, particle color, turbidity, particle concentration, micro-particle size and concentration, floc growth rate during flocculation, or floc settling of a liquid flow.

8. The method according to claim 1, wherein a flow of an aqueous liquid to be monitored is surface water, ground water, salt water, raw water, wastewater, or industrial process water.

9. The method according to claim 1, wherein a chemically treated aqueous flow of the aqueous liquid is directed to a separation unit, for a flotation, sedimentation, reverse osmosis, nanofiltration, ultrafiltration, or microfiltration process.

10. The method according to claim 7, wherein the at least one chemical is selected from:
    coagulants and flocculants, water-soluble salts or anionic, nonionic and cationic polyelectrolytes of univalent or multivalent cations, sodium, calcium, magnesium, iron, aluminum, natural products, starch, semi-synthetic polymers, cationic starch and synthetic polymers, acrylic polymers, polyamines, polyethylene oxides and allylic polymers, or a mixture thereof.

11. A system for monitoring and/or optimization of coagulation and/or flocculation in a water treatment process, the system comprising:
    a data processing unit and, functionally connected to said data processing unit:
        means for taking samples from an aqueous liquid;
        an imaging device configured to capture visual data of particles dispersed or suspended in said liquid; and
        means for controlling a dosage of at least one coagulation and/or flocculation agent to the water treatment process, wherein said data processing unit including a non-transitory computer readable medium having stored thereon a set of computer executable instructions for causing the data processing unit to perform steps of:
            classifying particle types based on said visual data;
            computing a particle size distribution indication for at least one classified particle type; and
            comparing said particle size distribution indication to a predetermined particle size distribution value;
        wherein said data processing unit is configured to carry out at least one of:

a) compute a particle size distribution indication for flocs, and compare the particle size distribution indication for flocs to a predetermined particle size distribution value;
b) compute a particle count for microparticles, and compare said particle count for microparticles to a predetermined particle count value; or
c) monitor the samples with the imaging device to capture visual data of compounds dissolved in the liquid, compute water color of the samples based on the visual data, and compare the computed water color to a predetermined water color value;

wherein said data processing unit is further configured to:
in response to a difference detected in any one or combination of the comparing steps, adjusting the dosage of at least one flocculation and/or coagulation agent for said particles to an aqueous liquid flow of the aqueous liquid to optimize the coagulation and/or flocculation of the particles dispersed or suspended in the liquid.

12. The system according to claim 11, wherein said data processing unit is configured to:
compute the particle count for particles having a particle size of 0.1 to 500 μm.

13. The system according to claim 11, wherein said data processing unit is configured to:
compute a particle size distribution indication for at least one of fiber, fluff, micro-particle, or microplastics; and compare said particle size distribution indication to a predetermined particle size distribution value.

14. The system according to claim 11, wherein said data processing unit is configured to:
compare the obtained visual data to stored reference data of shape factors and/or size of particles, in order to classify said particle types.

15. The system according to claim 14, wherein said data processing unit is configured to:
additionally compare the obtained visual data to stored reference data of color factors of particles, in order to classify said particle types.

16. The system according to claim 11, wherein said particle types comprise one or more of the following:
a floc, fiber, fluff, micro-particle, or microplastics.

17. The system according to claim 11, wherein said data processing unit is configured to:
adjust dosage of at least one chemical to the water treatment process based on a measurement from the captured visual data, the measurement comprising one or more of the following:
water color, particle color, turbidity, particle concentration, micro-particle size and concentration, floc growth rate during flocculation, or floc settling of said aqueous liquid flow.

18. The system according to claim 17 configured for a water treatment process to optimize coagulation and/or flocculation, wherein the at least one chemical is selected from:
coagulants and flocculants, water-soluble salts or anionic, nonionic and cationic polyelectrolytes of univalent or multivalent cations, sodium, calcium, magnesium, iron, aluminum, natural products, starch, semi-synthetic polymers, cationic starch and synthetic polymers, acrylic polymers, polyamines, polyethylene oxides and allylic polymers, or a mixture thereof.

19. The system according to claim 18, wherein an aqueous liquid to be monitored is surface water, ground water, salt water, raw water, wastewater, or industrial process water.

20. The system according to claim 18, wherein the chemically treated aqueous liquid flow is directed to a separation unit configured for a flotation, sedimentation, reverse osmosis, nanofiltration, ultrafiltration, or a microfiltration process.

21. The method according to claim 1, wherein the computing of the particle count for the microparticles comprises:
computing the particle count for particles having a particle size of 1 to 20 μm.

22. The system according to claim 11, wherein said data processing unit is configured to:
compute the particle count for particles having a particle size of 1 to 20 μm.

* * * * *